(12) United States Patent
Gupta et al.

(10) Patent No.: US 7,381,562 B2
(45) Date of Patent: Jun. 3, 2008

(54) METHODS FOR PRODUCING COTYLEDONARY PINE EMBRYOS UTILIZING A GIBBERELLIN

(75) Inventors: Pramod K. Gupta, Federal Way, WA (US); Diane Holmstrom, Sumner, WA (US); Bonnie Larson, Granite Falls, WA (US)

(73) Assignee: Weyerhaeuser Company, Federal Way, WA (US)

( * ) Notice: Subject to any disclaimer, the term of this patent is extended or adjusted under 35 U.S.C. 154(b) by 747 days.

(21) Appl. No.: 10/405,819

(22) Filed: Apr. 1, 2003

(65) Prior Publication Data

US 2003/0226165 A1   Dec. 4, 2003

(51) Int. Cl.
*C12N 5/00* (2006.01)
*C12N 5/04* (2006.01)
*A01H 4/00* (2006.01)

(52) U.S. Cl. .................................. 435/422; 435/430.1
(58) Field of Classification Search .................... 435/6
See application file for complete search history.

(56) References Cited

U.S. PATENT DOCUMENTS

| | | | |
|---|---|---|---|
| 4,217,730 A | 8/1980 | Abo El-Nil |
| 4,801,545 A | 1/1989 | Stuart et al. |
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,183,757 A | 2/1993 | Roberts |
| 5,187,092 A | 2/1993 | Uddin |
| 5,236,841 A | 8/1993 | Gupta et al. |
| 5,238,835 A | 8/1993 | McKersie et al. |
| 5,294,549 A * | 3/1994 | Pullman et al. ............. 435/422 |
| 5,413,930 A | 5/1995 | Becwar et al. |
| 5,464,769 A | 11/1995 | Attree et al. |
| 5,482,857 A | 1/1996 | Gupta et al. |
| 5,491,090 A | 2/1996 | Handley, III et al. |
| 5,501,972 A | 3/1996 | Westcott |
| 5,506,136 A | 4/1996 | Becwar et al. |
| 5,523,230 A | 6/1996 | Smith |
| 5,534,433 A | 7/1996 | Coke |
| 5,534,434 A | 7/1996 | Coke |
| 5,563,061 A | 10/1996 | Gupta |
| 5,564,224 A | 10/1996 | Carlson et al. |
| 5,565,355 A | 10/1996 | Smith |
| 5,587,312 A | 12/1996 | van Holst et al. |
| 5,610,051 A | 3/1997 | Becwar et al. |
| 5,677,185 A | 10/1997 | Handley, III |
| 5,731,191 A | 3/1998 | Rutter et al. |
| 5,731,203 A | 3/1998 | Handley, III |
| 5,731,204 A | 3/1998 | Rutter et al. |
| 5,821,126 A | 10/1998 | Durzan et al. |
| 5,840,581 A | 11/1998 | Carraway et al. |
| 5,850,032 A | 12/1998 | Wann |
| 5,856,191 A | 1/1999 | Handley, III |
| 5,985,667 A | 11/1999 | Attree et al. |
| 6,022,744 A | 2/2000 | Tetteroo et al. |
| 6,117,678 A | 9/2000 | Carpenter et al. |
| 6,134,830 A | 10/2000 | Welty |
| 6,150,167 A | 11/2000 | Carpenter et al. |
| 6,180,405 B1 | 1/2001 | Aitken-Christie et al. |
| 6,200,809 B1 | 3/2001 | Klimaszewska et al. |
| 6,340,594 B1 | 1/2002 | Attree et al. |
| 6,372,496 B1 | 4/2002 | Attree et al. |
| 6,417,001 B2 | 7/2002 | Aitken-Christie et al. |
| 6,444,467 B1 | 9/2002 | Fan et al. |
| 6,492,174 B1 | 12/2002 | Pullman et al. |
| 6,893,873 B2 * | 5/2005 | Pullman ..................... 435/422 |
| 2002/0012994 A1 | 1/2002 | Aitken-Christie et al. |
| 2002/0092037 A1 | 7/2002 | Connett-Porceddu et al. |
| 2002/0100083 A1 | 7/2002 | Connett-Porceddu et al. |

FOREIGN PATENT DOCUMENTS

| | | |
|---|---|---|
| AU | A-51613/90 A1 | 2/1990 |
| EP | 0 300 730 B1 | 1/1989 |
| EP | 0 618 766 B1 | 10/1994 |
| EP | 0 934 691 A2 | 8/1999 |
| WO | WO 95/33822 A1 | 12/1995 |
| WO | WO 98/48279 A1 | 10/1998 |
| WO | WO 01/20972 A1 | 9/2000 |

OTHER PUBLICATIONS

Hansen, G. et al. "Recent advances in the transformation of plants," Trends in Plant Science- Reviews, Jun. 1999, vol. 4, No. 6, pp. 226-231. (6 pages total).*

(Continued)

*Primary Examiner*—David H Kruse
*Assistant Examiner*—S. B. McCormick-Ewoldt
(74) *Attorney, Agent, or Firm*—Christensen O'Connor Johnson Kindness

(57) ABSTRACT

The present invention provides methods for producing cotyledonary pine embryos. The methods of the invention each include the step of culturing embryogenic pine tissue in, or on, a medium including at least one gibberellin to yield cotyledonary pine embryos. In some embodiments, an absorbent composition, such as activated charcoal, is included in the medium to further promote production of cotyledonary pine embryos.

19 Claims, No Drawings

OTHER PUBLICATIONS

Jain, S.M., et al., Forestry Sciences: Somatic Embryogenesis in Woody Plants, vol. 3, *Gymnosperms*, Kluwer Academic Publishers, Netherlands, 1995.

Timmis, R., "Bioprocessing for Tree Production in the Forest Industry: Conifer Somatic Embryogenesis," *Biotechnol. Prog.* 14(1):156-166, 1998.

Attree, S.M. et al., "Somatic Embryo Maturation, Germination, and Soil Establishment of Plants of Black and White Spruce (*Picea mariana* and *Picea glauca*)," *Can. J. Bot.* 68:2583-2589, 1990.

Attree, S.M., et al., "Initiation of Embryogenic Callus and Suspension Cultures, and Improved Embryo Regeneration of Protoplasts, of White Spruce (*Picea glauca*)," *Can. J. Bot.* 67:1790-1795, 1989.

Attree, S.M., et al., "Plantlet Regeneration From Embryogenic Protoplasts of White Spruce (*Picea glauca*)," *Bio/Technology* 7:1060-1062, 1989.

Bonga, J.M., et al., Forestry Sciences: Cell and Tissue Culture in Forestry, vol. 1, *General Principles and Biotechnology*, Martinus Nijhoff Publishers, Netherlands, 1987.

Bonga, J.M., et al., Forestry Sciences: Cell and Tissue Culture in Forestry, vol. 2, *Specific Principles and Methods: Growth and Developments*, Martinus Nijhoff Publishers, Netherlands, 1987.

Bonga, J.M., et al., Forestry Sciences: Cell and Tissue Culture in Forestry, vol. 3, *Case Histories: Gymnosperms, Angiosperms and Palms*, Martinus Nijhoff Publishers, Netherlands, 1987.

Boulay, M.P., et al., "Development of Somatic Embryos From Cell Suspension Cultures of Norway Spruce (*Picea abies* Karst.)," *Plant Cell Reports* 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Gupta, P.K., et al., "Scale-Up Somatic Embyrogenesis of Conifers For Reforestation," *Proceedings of the 3rd Canadian Workshop on Plant Tissue Culture and Genetic Engineering, University of Guelph, Symposium 1: Somatic Embryogenesis and Synthetic Seeds*, Abstract, Jun. 1992.

Hakman, I. and L.C. Fowke, "An Embryogenic Cell Suspension Culture of *Picea glauca* (White Spruce)," *Plant Cell Reports* 6:20-22, 1987.

Keinonen-Mettälä, K., et al., "Somatic Embryogenesis of *Pinus sylvestris*," *Scand. J. For. Res.* 11:242-250, 1996.

Krogstrup, P. "Somatic Embyrogenesis in Sitka Spruce (*Picea sitchensis* (Bong.) Carr.)," *Plant Cell Reports* 7:594-597, 1988.

Lelu, M.A. et al., "Effect of Maturation Duration on Desiccation Tolerance in Hybrid Larch (*Larix X leptoeuropaea dengler*) Somatic Embryos," *In Vitro Cell. Dev. Biol.* 3115-20, 1995.

Lu, C.-Y. and T.A. Thorpe, "Somatic Embryogenesis and Plantlet Regeneration in Cultured Immature Embryos of *Picea glauca*," *J. Plant Physiol.* 128:297-302, 1987.

Mathur, G. et al., "Studies on Somatic Embryogenesis From Immature Zygotic Embryos of CHIR Pine (*Pinus roxburghii* Sarg.)," *Current Science* 79(7):999-1004, 2000.

Norgaard, J.V., and P. Krogstrup, "Cytokinin Induced Somatic Embryogenesis From Immature Embryos of *Abies nordmanniana* Lk.," *Plant Cell Reports* 9:509-513, 1991.

Roberts, D.R., "Abscisic Acid and Mannitol Promote Early Development, Maturation and Storage Protein Accumulation in Somatic Embryos of Interior Spruce," *Physiologia Plantarum* 83:247-254, 1991.

Roberts, D.R., et al., "Interaction Between Maturation and High Relative Humidity Treatments and Their Effects on Germination of Sitka Spruce Somatic Embryos," *J. Plant Physiol.* 138:1-6, 1991.

Roberts, D.R., et al., "Synchronous and High Frequency Germination of Interior Spruce Somatic Embryos Following Partial Drying at High Relative Humidity," *Can. J. Bot.* 68:1086-1090, 1989.

Thompson, R.G. and P. von Aderkas, "Somatic Embryogenesis and Plant Regeneration From Mature Embryos of Western Larch," *Plant Cell Reports* 11:379-386, 1992.

von Aderkas, P., et al., "Charcoal Affects Early Development and Hormonal Concentrations of Somatic Embryos of Hybrid Larch," *Tree Physiology* 22:431-434, 2002.

von Arnold, S. and I. Hakman, "Regulation of Somatic Embryo Development in *Picea abies* by Abscisic Acid (ABA)," *J. Plant Physiol.* 132:164-169, 1988.

von Arnold, S. and T. Eriksson, "A Revised Medium for Growth of Pea Mesophyll Protoplasts," *Physiol. Plant* 39:257-260, 1977.

Webb, D.T., et al., "Factors Influencing the Induction of Embryogenic and Caulogenic Callus From Embros of *Picea glauca* and *P. engelmanii*," *Can. J. For. Res. 19*:1303-1308, 1989.

Chalupa V, "Plant regeneration by somatic embryogenesis from cultured immature embryos of oak (*Quercus robur* L.) and lindern (*Tiolia cordata* Mill.)," *Plant Cell Rep* 9:396-401 (1990).

Lakshmi SG, "Sandalwood (*Santalum album*)," *Biotechnology in Agriculture and Forestry 1: Trees 1, Y*, P S Bajaj, ed. Springer-velag, New York (1985).

\* cited by examiner

METHODS FOR PRODUCING COTYLEDONARY PINE EMBRYOS UTILIZING A GIBBERELLIN

FIELD OF THE INVENTION

The present invention relates to methods for producing plant embryos in vitro, and optionally producing plants from the plant embryos.

BACKGROUND OF THE INVENTION

The demand for pine trees to make wood products continues to increase. One proposed solution to this problem is to identify individual trees that possess desirable characteristics, such as a rapid rate of growth, and produce numerous, genetically identical, clones of the superior trees by somatic cloning. These clones can be cultivated to yield stands, or whole forests, of pine trees that possess the desirable characteristic(s).

One method for cloning pine trees utilizes in vitro treatment of isolated, living, pine tissue under conditions that promote formation of pine embryos, and then whole plants, from the treated tissue. The isolated pine tissue may be cultured in the presence of one or more auxins and/or cytokinins to promote formation and multiplication of embryogenic tissue to form cotyledonary pine embryos. The embryos may then be germinated and grown to yield pine trees.

A continuing problem, however, is stimulating efficient formation of cotyledonary pine embryos that are capable of germinating to yield pine plants. Preferably the cotyledonary pine embryos, formed in vitro, are physically and physiologically similar, or identical, to zygotic pine embryos formed, in vivo, in pine seeds. There is therefore a need for methods for producing cotyledonary pine embryos from pine embryogenic tissue. The present invention provides methods that satisfy this need.

SUMMARY OF THE INVENTION

In one aspect, the present invention provides methods for producing cotyledonary pine embryos. The methods of the invention each include the step of culturing embryogenic pine tissue in, or on, a medium including at least one gibberellin to yield cotyledonary pine embryos. In some embodiments, the embryogenic tissue is cultured in, or on, a medium that does not comprise at least one gibberellin, after the embryogenic tissue has been cultured in, or on, a medium comprising at least one gibberellin. The medium that does not comprise a gibberellin may be adapted to promote the development and maturation of cotyledonary pine embryos from gibberellin-treated embryogenic pine tissue.

In some embodiments, the present invention provides methods for producing cotyledonary pine embryos, the methods each including the steps of: (a) culturing pine embryonal suspensor masses on solid maintenance medium that does not comprise a gibberellin; (b) culturing the pine embryonal suspensor masses treated in accordance with step (a) in liquid maintenance medium that does not comprise a gibberellin; (c) culturing the pine embryonal suspensor masses treated in accordance with step (b) in a liquid maintenance medium comprising at least one gibberellin; and (d) culturing the pine embryonal suspensor masses treated in accordance with step (c) on solid development medium, that does not comprise a gibberellin, to yield cotyledonary pine embryos.

The methods of the invention each yield more cotyledonary pine embryos than an identical method that does not utilize a gibberellin. Some embodiments of the methods of the invention yield at least 50% more cotyledonary pine embryos (such as at least 75% more cotyledonary pine embryos, or such as at least 100% more cotyledonary pine embryos) than an identical method for producing cotyledonary pine embryos that does not utilize a gibberellin.

The methods of the present invention are useful for preparing cotyledonary pine embryos that can be further characterized, such as by genetic or biochemical means, and/or can be germinated to yield small pine plants that can be grown into mature pine trees, if so desired. Thus, for example, the methods of the invention can be used to produce clones of individual pine trees that possess one or more desirable characteristics, such as a rapid growth rate or improved wood quality. For example, a population of cotyledonary pine embryos of the invention can be used to produce a stand, or forest, of pine trees possessing one or more desirable characteristics, such as a rapid growth rate or improved wood quality. The trees can be utilized to produce wood products.

DETAILED DESCRIPTION OF THE PREFERRED EMBODIMENT

Unless specifically defined herein, all terms used herein have the same meaning as they would to one skilled in the art of the present invention.

As used herein, the term "cotyledonary embryo" means an embryo that possesses one or more cotyledons.

As used herein, the term "embryogenic tissue" refers to any tissue, derived from a plant of the family Pinacea, that is capable of producing one or more cotyledonary pine embryos when treated in accordance with the methods of the invention. Thus, the term "embryogenic tissue" includes, for example, pine embryonal suspensor masses.

Unless stated otherwise, all concentration values that are expressed as percentages are weight per volume percentages.

In one aspect, the present invention provides methods for producing cotyledonary pine embryos. The methods of the invention each include the step of culturing embryogenic pine tissue in, or on, a medium including at least one gibberellin to yield cotyledonary pine embryos. In some embodiments of the methods of the invention, the gibberellin-treated embryogenic pine tissue is then cultured in, or on, at least one other medium to produce cotyledonary pine embryos. The methods of the invention can be used to produce cotyledonary embryos from any member of the family Pinacea, such as members of the genus Pinus, such as Loblolly pine (*Pinus taeda*).

An example of embryogenic tissue useful in the practice of the present invention is embryonal suspensor masses (ESMs). ESMs can be prepared from precotyledonary embryos removed from pine seed. The seed are typically surface sterilized before removing the precotyledonary embryos which are then cultured on, or in, medium that permits formation of ESMs which include early stage embryos in the process of multiplication by budding and cleavage. The medium may, if desired, include hormones that stimulate multiplication of the early stage embryos. Examples of hormones that can be included in the medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L. An example of a medium useful for culturing pine precotyledonary embryos to induce formation of ESMs is medium $BM_1$ set forth in Example 1 herein.

In the practice of the methods of the invention, embryogenic pine tissue is cultured in, or on, a medium including at least one gibberellin under conditions that yield cotyledonary pine embryos. Gibberellins are a class of art-recognized, diterpenoid plant hormones (see, e.g., Gibberellins and Plant Growth, by H. N. Krishnamoorthy, John Wiley & Sons (1975), which publication is incorporated herein by reference in its entirety). Representative examples of gibberellins useful in the practice of the present invention include gibberellic acid, gibberellin 4 and gibberellin 7 which are each disclosed, for example, in the aforementioned Krishnamoorthy text book. An example of a useful mixture of gibberellins is a mixture of gibberellin 4 and gibberellin 7 (referred to as gibberellin 4/7), such as the gibberellin 4/7 sold by Abbott Laboratories, Chicago, Ill.

The concentration of gibberellin(s) in the medium is sufficient to induce formation of cotyledonary pine embryos. In some embodiments of the methods of the invention, the concentration of gibberellin(s) in the medium is between 0.5 mg/L and 500 mg/L. In some embodiments of the methods of the invention, the concentration of gibberellin(s) in the medium is between 1 mg/L and 100 mg/L. In some embodiments of the methods of the invention, the concentration of gibberellin(s) in the medium is between 5 mg/L and 50 mg/L. In those embodiments of the methods of the invention in which more than one gibberellin is present in the medium, the foregoing concentration ranges refer to the total gibberellin concentration in the medium.

In some embodiments of the methods of the invention, embryogenic pine tissue is cultured in, or on, a medium including at least one gibberellin from a period of from 0.5 weeks to 5 weeks, such as from one week to three weeks, or such as from one week to two weeks. In some embodiments of the methods of the invention, embryogenic pine tissue is cultured in, or on, a medium including at least one gibberellin at a temperature of from 10° C. to 30° C., such as from 15° C. to 25° C., or such as from 20° C. to 23° C.

The medium including at least one gibberellin can be a liquid medium or a solid medium. When a liquid medium is utilized, the embryogenic tissue may be completely immersed in the medium which may be agitated during the time that the embryogenic tissue is cultured therein. When a solid medium is utilized, the embryogenic tissue may be placed on the surface of the medium, and may partially penetrate the surface of the solid medium. Thus, solid media include media that are partially solidified and permit the embryogenic tissue to substantially penetrate into the body of the medium, and also include fully solidified media that do not permit the embryogenic tissue to penetrate the body of the solidified medium. Liquid media can be completely or partially solidified by addition of an appropriate amount of a gellant, such as agar.

The medium that includes at least one gibberellin also may include nutrients that sustain the incubated plant tissue, and one or more agents for adjusting the osmolality of the medium to within a desired range. For example, the osmolality of the medium may be from 90 mM/Kg to 300 mM/Kg, such as from 100 mM/Kg to 200 mM/Kg, or such as from 100 mM/Kg to 150 mM/Kg. The pH of the medium can also be adjusted to a desired value. For example, the pH of the medium may be from 4.5 to 6.0, or, for example, from 5.0 to 6.0. Maltose may be included in the medium as the principal or sole source of metabolizable sugar for the embryogenic tissue. Useful maltose concentrations are within the range of from 1% to 2.5%.

The methods of the invention each yield more cotyledonary pine embryos than an identical method that does not utilize a gibberellin. Some embodiments of the methods of the invention yield at least 50% more cotyledonary pine embryos (such as at least 75% more cotyledonary pine embryos, or such as at least 100% more cotyledonary pine embryos, or such as at least 150% more cotyledonary pine embryos) than an identical method for producing cotyledonary pine embryos that does not utilize a gibberellin. Thus, for example, some embodiments of the methods of the invention yield from 50% to 200% more cotyledonary pine embryos than an identical method for producing cotyledonary pine embryos that does not utilize a gibberellin. Again by way of example, some embodiments of the methods of the invention yield from 50% to 150% more cotyledonary pine embryos than an identical method for producing cotyledonary pine embryos that does not utilize a gibberellin.

It has been found that the inclusion of an absorbent composition in the medium including one or more gibberellins further enhances production of cotyledonary pine embryos. The absorbent composition can be any composition that is not toxic to the embryogenic tissue at the concentrations utilized in the practice of the present methods, and that is capable of absorbing growth-promoting hormones, and toxic compounds produced by the plant cells during embryo development, that are present in the medium. Thus, the absorbed hormone(s) is/are no longer available to promote the growth of the embryogenic tissue in, or on, the medium; and the absorbed toxins cannot adversely affect the plant cells. In this context, the term "absorbing" encompasses any chemical or physical interaction between the absorbent composition and one or more growth-promoting hormones, and/or toxins, in the medium, so that the growth-promoting hormone(s), and/or toxins, are bound to the absorbent composition.

Thus, in some embodiments of the methods of the invention, the embryogenic tissue is incubated in, or on, a medium that includes growth-promoting hormones, such as auxins and/or cytokinins, to promote multiplication of the embryogenic tissue. When sufficient embryogenic tissue has been obtained, the embryogenic tissue may then be transferred to medium that does not include growth-promoting hormones, but includes one or more gibberellins and, optionally, one or more absorbent compositions. In other embodiments, one or more gibberellins and, optionally, one or more absorbent compositions may be added directly to the medium that includes one or more growth-promoting hormones. In either situation, the absorbent composition(s) bind growth-promoting hormones present in the medium so that the rate of multiplication of the embryogenic tissue is reduced, or multiplication is stopped entirely, and the gibberellin(s) induce production of a population of cotyledonary pine embryos from the embryogenic tissue.

Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from 0.1 g/L to 5 g/L. In some embodiments, the absorbent composition is present in an amount of from 0.5 g/L to 1 g/L. In those embodiments of the methods of the invention in which more than one absorbent composition is present in the medium, the foregoing concentration ranges refer to the total absorbent composition concentration in the medium.

In the practice of some embodiments of the invention, the embryogenic tissue is sequentially cultured on, or in, a series of at least two media, at least one of which includes a gibberellin. Thus, in some embodiments, the present invention provides methods for producing cotyledonary pine embryos, the methods each including the steps of (a) culturing embryogenic pine tissue in, or on, a medium comprising at least one gibberellin to yield cultured embryogenic tissue; and then (b) further culturing the cultured embryogenic tissue prepared in accordance with step (a) in, or on, a medium that does not comprise at least one gibberellin, to yield cotyledonary pine embryos. Thus, the medium that does not include a gibberellin is adapted to promote the development and maturation of cotyledonary pine embryos from gibberellin-treated embryogenic tissue.

For example, in the practice of some embodiments of the methods of the invention, embryogenic pine tissue (such as ESM) is cultured on, or in, a maintenance medium that is adapted to promote cell division and growth of the embryogenic tissue. The maintenance medium can be a solid medium, or a liquid medium which can be agitated to promote growth and multiplication of the embryogenic tissue therein. The maintenance medium does not include a gibberellin, but may contain nutrients that sustain the embryogenic tissue, and may include hormones, such as one or more auxins and/or cytokinins, that promote cell division and growth of the embryogenic tissue. If auxin is utilized, the concentration of auxin within the maintenance medium can be, for example, from 0.1 mg/L to 10 mg/L (such as from 0.1 mg/L to 5 mg/L). If more than one auxin is present in the medium, the foregoing concentration ranges refer to the total auxin concentration in the medium. If a cytokinin is utilized, the concentration of cytokinin within the maintenance medium can be, for example, from 0.1 mg/L to 2 mg/L (such as from 0.1 mg/L to 1 mg/L). If more than one cytokinin is present in the medium, the foregoing concentration ranges refer to the total cytokinin concentration in the medium.

It is generally desirable, though not essential, to include maltose as the sole, or principal, metabolizable sugar source in the maintenance medium. Useful maltose concentrations are within the range of from 1% to 2.5%. The osmolality of the maintenance medium can be adjusted to a value that falls within a desired range, such as from 90 mM/Kg to 300 mM/Kg, or such as from 100 mM/Kg to 200 mM/Kg, or such as from 100 mM/Kg to 150 mM/Kg. The pH of the medium can also be adjusted to a desired value. For example, the pH of the medium may be from 4.5 to 6.0. The embryogenic tissue is typically incubated in, or on, the maintenance medium at a temperature in the range of from 10° C. to 30° C., such as from 15° C. to 25° C., or such as from 20° C. to 23° C. An example of a suitable maintenance medium is medium $BM_2$ set forth in Example 1 herein. The embryogenic tissue is incubated in the maintenance medium until the embryogenic tissue has multiplied by a desired amount (as determined, for example, by the length of the cultured embryogenic tissue).

After the embryogenic tissue has multiplied by a desired amount, one or more gibberellins may be added to the maintenance medium (or the embryogenic tissue may be transferred to a different maintenance medium containing one or more gibberellins, or to a fresh aliquot of the same maintenance medium containing one or more gibberellins) to induce production of cotyledonary pine embryos. In addition to one or more gibberellins, the maintenance medium can also include an absorbent composition.

The gibberellin(s) can be present in the maintenance medium at a concentration between 0.5 mg/L and 500 mg/L, such as from 1 mg/L to 100 mg/L, or such as from 5 mg/L to 50 mg/L. The absorbent composition(s) can be present in the maintenance medium at a concentration, for example, between 0.1 g/L and 5 g/L, such as from 0.5 g/L to 1 g/L. The osmolality of the maintenance medium, that includes one or more gibberellins, can be adjusted to a value that falls within a desired range, such as from 90 mM/Kg to 300 mM/Kg, or such as from 100 mM/Kg to 200 mM/Kg, or such as from 100 mM/Kg to 150 mM/Kg. The pH of the maintenance medium can also be adjusted to a desired value. For example, the pH of the maintenance medium may be from 4.5 to 6.0. The embryogenic tissue is typically incubated in, or on, the maintenance medium, that includes one or more gibberellins, at a temperature in the range of from 10° C. to 30° C., such as from 15° C. to 25° C., or such as from 20° C. to 23° C.

The embryogenic tissue is typically incubated in the maintenance medium, in the presence of one or more gibberellins, and optionally one or more absorbent compositions, for a period of from 0.5 weeks to 5 weeks, such as from one week to three weeks, or such as from one week to two weeks.

The gibberellin-treated embryogenic tissue can then be transferred to a development medium adapted to promote development of cotyledonary pine embryos. The development medium is typically a solid medium, although the development medium can be a liquid medium. The development medium does not include a gibberellin (although some residual gibberellin may be transferred into the development medium with the embryogenic tissue). The development medium may contain nutrients that sustain the embryogenic tissue. Maltose may be included in the medium as the principal or sole source of sugar for the embryogenic tissue. Useful maltose concentrations are within the range of from 1% to 2.5%.

Suitable development media typically do not include growth-promoting hormones, such as auxins and cytokinins, but may include the hormone abscisic acid. When abscisic acid is utilized in the development medium, it is typically utilized at a concentration in the range of from 1 mg/L to 200 mg/L, such as from 1 mg/L to 100 mg/L. The osmolality of the development medium can be adjusted to a value that falls within a desired range, such as from 250 mM/Kg to 450 mM/Kg, or such as from 250 mM/Kg to 350 mM/Kg. The pH of the development medium may also be adjusted to a value within a desired range, such as from 4.5 to 6.5, or such as from 5.0 to 6.0. The embryogenic tissue is typically incubated in, or on, the development medium at a temperature in the range of from 20° C. to 24° C., such as from 21° C. to 24° C. An example of a suitable development medium is medium $BM_3$ set forth in Example 1 herein. In some embodiments of the methods of the invention, embryogenic tissue is incubated in, or on, the development medium for a period of from six weeks to twelve weeks, such as from six weeks to nine weeks.

Thus, in some embodiments, the present invention provides methods for producing cotyledonary pine embryos, the methods each including the steps of: (a) culturing embryogenic pine tissue (such as pine embryonal suspensor masses) on solid maintenance medium; then (b) culturing the embryogenic pine tissue in liquid maintenance medium; then (c) culturing the embryogenic pine tissue in liquid maintenance medium comprising a gibberellin; (and optionally an absorbent composition); and then (d) culturing the embryogenic pine tissue on solid development medium to form cotyledonary pine embryos. In the practice of these embodiments of the methods of the invention, only the liquid maintenance medium utilized in step (c) comprises a gibberellin. The methods of this aspect of the invention may optionally include the step of culturing pine tissue in, or on, an initiation medium to yield embryogenic pine tissue, which is then cultured in, or on, a maintenance medium as set forth in step (a).

The cotyledonary pine embryos produced using the methods of the invention can optionally be germinated to form pine plants which can be grown into pine trees, if desired. The cotyledonary pine embryos can be germinated on a solid germination medium, such as medium $BM_4$ medium set forth in Example 1 herein. The germinated plants can be transferred to soil for further growth. For example, the germinated plants can be planted in soil in a greenhouse and allowed to grow before being transplanted to an outdoor site. Typically, the cotyledonary pine embryos are illuminated to stimulate germination. Typically, all the steps of the methods of the invention, except germination, are conducted in the dark.

The methods of the invention can be used, for example, to produce clones of individual pine trees that possess one or more desirable characteristics, such as a rapid growth rate. Thus, in one aspect, the present invention provides methods for producing a population of genetically-identical, cotyledonary pine embryos. The methods of this aspect of the invention each include the step of culturing genetically-identical embryogenic pine tissue in, or on, a medium including at least one gibberellin to yield a population of cotyledonary pine embryos. Any of the methods described herein can be used to produce populations of genetically-identical, cotyledonary pine embryos.

The following examples merely illustrate the best mode now contemplated for practicing the invention, but should not be construed to limit the invention.

EXAMPLE 1

This Example shows a representative method of the invention for producing Loblolly pine (*Pinus taeda*), cotyledonary embryos.

Female gametophytes containing zygotic embryos are removed from seeds four to five weeks after fertilization. The seed coats are removed but the embryos are not further dissected out of the surrounding gametophyte other than to excise the nucellar end. The cones are stored at 4° C. until used. Immediately before removal of the immature embryos the seeds are sterilized utilizing an initial washing and detergent treatment followed by a ten minute sterilization in 15% $H_2O_2$. The explants are thoroughly washed with sterile distilled water after each treatment.

Tables 1 and 2 set forth the compositions of media useful for producing loblolly pine cotyledonary embryos in accordance with the methods of the invention.

TABLE 1

*Pinus Taeda* Basal Medium (BM)

| Constituent | Concentration (mg/L) |
|---|---|
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 13.9 |
| $Na_2EDTA$ | 18.65 |
| Sucrose | 30,000. |
| myo-Inositol | 100 |
| Casamino acids | 500 |
| L-Glutamine | 1000 |
| Thiamine•HCl | 1.00 |
| Pyridoxine•HCl | 0.50 |
| Nicotinic acid | 0.50 |
| Glycine | 2.00 |
| Agar[+] | 6,000 |
| pH adjusted to 5.7 | |

[+]Used if a solid medium is desired

TABLE 2

Composition of Media for Different Stage Treatments

| | |
|---|---|
| $BM_1$—Induction Medium | BM + 2,4-D (15 μM) + Kinetin (2 μM) + BAP (2 μM) |
| $BM_2$—Maintenance and Multiplication Medium | BM + 2,4-D (5 μM) + Kinetin (0.5 μM) + BAP (0.5 μM) + 4900 mg/L additional myo-inositol. Maltose is substituted for sucrose on an equal weight basis. Agar is added when a solid medium is desired. |
| $BM_3$—Cotyledonary Embryo Development Medium | BM + 50 mg/L abscisic acid + 18% PEG-4000 & 8000 mixture + 2.5% maltose + 900 mg/L additional myo-inositol + 1000 mg/L glutamine + 0.125% activated charcoal. No gellant. The following amino acid mixture is added: L-proline (100 mg/L), L-asparagine (100 mg/L), L-arginine (50 mg/L), L-alanine (20 mg/L), and L-serine (20 mg/L). |
| $BM_4$—Germination Medium | BM modified by reducing sucrose to 20,000 mg/L, myo-inositol to 100.0 mg/L, glutamine and casamino acids to 0.0 mg/L + 0.6% agar and 0.25% activated charcoal. |

Stage 1—Induction:

Sterile gametophytes with intact embryos are placed on a solid $BM_1$ culture medium and held in an environment at 22°-25 C. with a 24 hour dark photoperiod for a time of 3-5 weeks. The length of time depends on the particular genotype being cultured. At the end of this time a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 170 mM/kg. Normally it is about 160 mM/kg or even lower (such as 150 mM/kg).

Stage II—Maintenance, Multiplication and Treatment with a Gibberellin:

Early stage embryos removed from the masses generated in the induction stage are first placed on a $BM_2$ gelled maintenance and multiplication medium. This differs from the induction medium in that the growth hormones (both auxins and cytokinins) are reduced by at least a full order of magnitude. Osmolality of this medium is typically raised from that of the induction medium to about 180 mM/kg or higher (typically within the range of about 180-400 mM/kg for *Pinus taeda*) by increasing the concentration of myo-inositol to 0.5% w/v. The temperature and photoperiod are again 22°-25 C. with 24 hours in the dark. Embryos are cultured 12-14 days on the $BM_2$ solid medium before transferring to a liquid medium for further subculturing. This liquid medium has the same composition as $BM_2$, but lacks the gellant. The embryos at the end of the solid maintenance stage are typically similar in appearance to those from Stage I. After 5 to 6 weekly subcultures on the liquid maintenance medium advanced early stage embryos have formed. These are characterized by smooth embryonal heads, estimated to typically have over 100 individual cells, with multiple suspensors.

The advanced early stage embryos are transferred to another maintenance medium having the composition of $BM_2$, but lacking 2,4-D, kinetin and BAP, and including GA 4/7 at a concentration of from 2.5 mg/L to 10.0 mg/L. The embryos are incubated in this medium for a period of from seven to fourteen days.

Stage III—Embryo Development

The advanced early stage embryos from Stage II culture are transferred to a filter paper support placed on a pad saturated with liquid development medium. This medium either lacks growth hormones entirely, or has them present only at very low levels, and has the same lower level of osmoticants as Stages I and II. Abscisic acid is typically included to facilitate further development. The further inclusion of an absorbent composition in this medium is advantageous. The absorbent composition may be chosen from a number of chemical materials having high surface area and/or controlled pore size, such as activated charcoal, soluble and insoluble forms of poly(vinyl pyrrolidone), activated alumina, and silica gel. The absorbent composition is normally present at a concentration of about 0.1-5 g/L, more generally about 0.25-2.5 g/L.

The osmotic potential of this development medium may be raised substantially over that of the maintenance medium. It has been found advantageous to have an osmolality as high as 350 mM/kg or even higher. Development is preferably carried out in complete darkness at a temperature of 22°-25 C. until elongated cotyledonary embryos have developed. Development time is typically several weeks, such as 10 to 12 weeks.

Stage IV—Drying

The embryos still on their filter paper support are lifted from the pad and placed in a closed container over a saturated solution of $K_2SO_4$, at a relative humidity of 97%, for a period of about three weeks.

Stage V—Germination

The dried cotyledonary embryos from Stage IV are rehydrated by placing them, while still on the filter paper support, for about 24 hours on a pad saturated with liquid germination medium. The embryos are then placed individually on solid $BM_4$ medium for germination. This is a basal medium lacking growth hormones which has been modified by reducing sucrose, myo-inositol and organic nitrogen. The embryos are incubated on $BM_4$ medium for about 6-8 weeks under environmental conditions of 23°-25° C., and a 16 hour light-8 hour dark photoperiod, until the resulting plantlets have a well developed radicle and hypocotyl and green cotyledonary structure and epicotyl.

Because of the reduced carbohydrate concentration, the osmotic potential of the germination medium is further reduced below that of the development medium. It is normally below about 150 mM/kg (such as about 100 mM/kg).

Stage VI—Conversion

Plantlets from Stage V are removed from the germination medium and planted in a soil comprising equal parts of peat and fine perlite.

EXAMPLE 2

This Example shows that gibberellin promotes the formation of loblolly pine somatic embryos.

Aliquots of ESM of Loblolly pine genotypes LP 7 and LP 5 were removed from maintenance cultures in medium 8280 and incubated in the media set forth in Table 3, before being transferred to development medium.

TABLE 3

| Medium Name and Composition | Culture Period Before Plating on Development Medium |
| --- | --- |
| 8280 (regular maintenance medium) | Three weeks |
| 8510 (8280 without hormones, plus 10 mg/L GA 4/7) | One week |
| 8511 (8280 without hormones plus 5.0 mg/L GA 4/7) | Two weeks |
| 8511 (8280 without hormones plus 5.0 mg/L GA 4/7) | One week |
| 8520 (8280 without hormones plus 2.5 mg/L GA 4/7) | Two weeks |

The treated ESM were rinsed with medium 8353 prior to plating onto development medium 8384 (including 50 mg/L abscisic acid). 0.75 ml of each culture (0.5 ml settled cells and 0.25 ml rinse medium 8353) was plated onto development medium.

Observations were made at the time of plating and approximately 12 weeks after plating. Good quality cotyledonary embryos were counted through the lid of the culture dishes and descriptions of embryo quality, such as embryo size, length, color and shape, were made prior to moving the embryos to stratification medium 8483 before drying and germination.

Table 4 shows the average yields of cotyledonary embryos for each genotype and treatment.

| Treatment | | | Genotype 5 | | Genotype 7 | |
| --- | --- | --- | --- | --- | --- | --- |
| Week | Shake | Development | Average | Std. Error | Average | Std. Error |
| 2 | 8280 | 8384 | 145 | 21.4 | 121 | 20.7 |
| 2 | 8511 | 8384 | 211 | 16.9 | 221 | 14.7 |
| 2 | 8520 | 8384 | 147 | 14.4 | 140 | 11.1 |

| Week | Shake Treatment | Average | Std. Error |
| --- | --- | --- | --- |
| 2 | 8280 (No GA) | 137 | 8.95 |
| 2 | 8511 (High GA) | 224 | 8.95 |
| 2 | 8520 (Low GA) | 187 | 8.95 |

The data show that culturing the Loblolly pine ESMs in a maintenance medium that includes a gibberellin (GA 4/7) increased the number, and improved the quality, of the cotyledonary embryos that formed after the ESMs were transferred to development medium. Cotyledonary embryos were larger, longer, more symmetrical and more organized.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for increasing the yield of Loblolly pine cotyledonary embryos, said method comprising the steps of:
   (a) culturing embryogenic Loblolly pine tissue on solid maintenance medium that does not comprise a gibberellin;
   (b) culturing the embryogenic pine tissue treated in accordance with step (a) in liquid maintenance medium that does not comprise a gibberellin;
   (c) culturing the embryogenic pine tissue treated in accordance with step (b) in a liquid maintenance medium comprising at least one gibberellin, provided that the liquid maintenance medium comprising a gibberellin does not comprise abscisic acid; and
   (d) culturing the embryogenic pine tissue treated in accordance with step (c) on solid development medium that does not comprise a gibberellin to yield a greater number of cotyledonary pine embryos than the number produced by culturing the embryogenic pine tissue in the liquid media of step (c) that does not comprise a gibberellin.

2. The method of claim 1 wherein the embryogenic pine tissue comprises embryonal suspensor masses.

3. The method of claim 1 wherein the embryogenic pine tissue consists of embryonal suspensor masses.

4. The method of claim 1 wherein the concentration of the at least one gibberellin in the liquid maintenance medium of step (c) is from 0.5 mg/L to 500 mg/L.

5. The method of claim 1 wherein the concentration of the at least one gibberellin in the liquid maintenance medium of step (c) is from 1.0 mg/L to 100 mg/L.

6. The method of claim 1 wherein the concentration of the at least one gibberellin in the liquid maintenance medium of step (c) is from 5 mg/L to 50 mg/L.

7. The method of claim 1 wherein the embryogenic pine tissue is cultured in, or on, the liquid maintenance medium of step (c) comprising at least one gibbereilin for a period of from 0.5 week to 5 weeks.

8. The method of claim 1 wherein the embryogenic pine tissue is cultured in, or on, the liquid maintenance medium of step (c) comprising at least one gibberellin for a period of from 1 week to 3 weeks.

9. The method of claim 1 wherein the embryogenic pine tissue is cultured in, or on, the liquid maintenance medium of step (c) comprisino at least one gibberellin for a period of from 1 week to 2 weeks.

10. The method of claim 1 wherein the osmolality of the liquid maintenance medium of step (c) comprising at least one gibberellin is from 90 mM/Kg to 300 mM/Kg.

11. The method of claim 1 wherein the pH of the liquid maintenance medium of step (c) comprising at least one gibberellin is from 4.5 to 6.0.

12. The method of claim 1 wherein the pH of the liquid maintenance medium of step (c) comprising at least one gibberellin is from 5.0 to 6.0.

13. The method of claim 1 wherein the liquid maintenance medium of step (c) comprising at least one gibberellin further comprises maltose present at a concentration of from 1% to 2.5%.

14. The method of claim 1 wherein the liquid maintenance medium of step (c) comprising at least one gibbereilin further comprises an absorbent composition.

15. The method of claim 14 wherein the absorbent composition is selected from the group consisting of activated charcoal, soluble poly(vinyl pyrrolidone), insoluble poly(vinyl pyrrolidone), activated alumina, and silica gel.

16. The method of claim 14 wherein the absorbent composition is activated charcoal.

17. The method of claim 14 wherein the concentration of the absorbent composition is from 0.1 g/L to 5 g/L.

18. The method of claim 14 wherein the concentration of the absorbent composition is from 0.5 g/L to 1 g/L.

19. The method of claim 1 wherein:
   the Loblolly pine embryogenic tissue according to step (a) consists essentially of embryonal suspensor masses;
   the concentration of the at least one gibberellin in the liquid maintenance medium according to step (c) is from 0.5 mg/L. to 500 mg/L; and
   the liquid maintenance medium according to step (c) further comprises an absorbent composition present at a concentration of from 0.1 g/L to 5 g/L.

* * * * *